US011421200B2

(12) United States Patent
Kim et al.

(10) Patent No.: US 11,421,200 B2
(45) Date of Patent: Aug. 23, 2022

(54) **MICROORGANISM OF THE GENUS *CORYNEBACTERIUM* PRODUCING PURINE NUCLEOTIDE AND A METHOD FOR PRODUCING PURINE NUCLEOTIDE BY USING THE SAME**

(71) Applicant: CJ CHEILJEDANG CORPORATION, Seoul (KR)

(72) Inventors: Hee Ju Kim, Seoul (KR); Bo Ram Lim, Seoul (KR); Byoung Hoon Yoon, Seoul (KR); Min Ji Baek, Seoul (KR); Ji Hye Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 52 days.

(21) Appl. No.: 16/960,449

(22) PCT Filed: Jan. 25, 2019

(86) PCT No.: PCT/KR2019/001117
§ 371 (c)(1),
(2) Date: Jul. 7, 2020

(87) PCT Pub. No.: WO2019/147078
PCT Pub. Date: Aug. 1, 2019

(65) Prior Publication Data
US 2020/0347346 A1    Nov. 5, 2020

(30) Foreign Application Priority Data

Jan. 25, 2018 (KR) ........................ 10-2018-0009632

(51) Int. Cl.
*C12N 1/20* (2006.01)
*C12P 19/32* (2006.01)

(52) U.S. Cl.
CPC ............... *C12N 1/20* (2013.01); *C12P 19/32* (2013.01)

(58) Field of Classification Search
CPC .......... C07K 14/34; C12N 15/77; C12N 1/20; C12P 19/32
See application file for complete search history.

(56) References Cited

U.S. PATENT DOCUMENTS

| | | | | |
|---|---|---|---|---|
| 2002/0197605 | A1* | 12/2002 | Nakagawa ............... | C12P 13/08 435/6.15 |
| 2007/0059809 | A1 | 3/2007 | Pompejus et al. | |
| 2015/0329883 | A1* | 11/2015 | Chung ...................... | C12P 7/46 435/252.32 |
| 2016/0222394 | A1 | 8/2016 | Yamada et al. | |
| 2021/0047666 | A1 | 2/2021 | Lee et al. | |

FOREIGN PATENT DOCUMENTS

| | | |
|---|---|---|
| JP | 2003-219876 A | 8/2003 |
| KR | 2002-0040602 A | 5/2002 |
| KR | 1020050043979 A | 5/2005 |
| KR | 2005-0056670 A | 6/2005 |
| KR | 1020050056670 A | 6/2005 |
| KR | 10-0588577 B1 | 6/2006 |
| KR | 1020070056491 A | 6/2007 |
| KR | 1020080025355 A | 3/2008 |
| KR | 1020100109732 A | 10/2010 |
| KR | 10-1049023 B1 | 7/2011 |
| KR | 10-1056872 B1 | 8/2011 |
| KR | 10-1210704 B1 | 12/2012 |
| KR | 101904675 B1 | 9/2018 |
| KR | 101950141 B1 | 2/2019 |
| RU | 2 209 249 C2 | 7/2003 |
| RU | 2 482 198 C1 | 5/2013 |
| WO | 2006/059877 A1 | 6/2006 |
| WO | 2008/033001 A1 | 3/2008 |

OTHER PUBLICATIONS

Alam et al., "Molecular function of WhiB4/Rv3681c of *Mycobacterium tuberculosis* H37Rv: a [4Fe-4S] cluster co-ordinating protein disulphide reductase," *Molecular Microbiology* 63(5):1414-1431 (2007).
GenBank: CP016326.1, Corynebacterium stationis strain ATCC 21170 genome, 533 pages, Jul. 5, 2017.
Ishii et al., "Improved Inosine Production and Derepression of Purine Nucleotide Biosynthetic Enzymes in 8-Azaguanine Resistant Mutants of *Bacillus subtilis*," *Agr. Biol. Chem.* 36(9):1511-1522 (1972).
Smith et al., "Structure of the Allosteric Regulatory Enzyme of Purine Biosynthesis," *Science* 264:1427-1433 (Jun. 3, 1994).
Database Patric [Online] Virginia Tech Cyberinfrastructure Division; Apr. 6, 2016 "Amidophosphoribosyltransferase (EC 2.4.2.14)" XP002801462 retrieved from Bacterial Bioinformatics Resource Center, Database Accession No. fig | 077974.3.peg.3565 (1 page).
Supplementary European Search Report corresponding to EP Application No. EP 19 76 2700, 7 pages, dated Jan. 11, 2021.
GenBank: KQB83970.1, Amidophosphoribosyltransferase precursor [Corynebacterium lowii] (2 pages) (Oct. 23, 2015).
GenBank: STC68793.1, amidophosphoribosyltransferase [Corynebacterium pilosum] (1 page) (Jul. 30, 2018).
Examination report No. 1 for standard patent application, corresponding to Australian Application No. 2019226146, 17 pages, dated Feb. 9, 2021.
GenBank: APT94087.1, WhiB family transcriptional regulator [Corynebacterium stationis], 2 pages (Jan. 10, 2017).
Peifer et al., "Metabolic engineering of the purine biosynthetic pathway in *Corynebacterium glutamicum* results in increased intracellular pool sizes of IMP and hypoxanthine," *Microbial Cell Factories* 11(138):1-14 (2012).

\* cited by examiner

*Primary Examiner* — Blaine Lankford
(74) *Attorney, Agent, or Firm* — Seed IP Law Group LLP

(57) ABSTRACT

The present disclosure relates to a microorganism of the genus *Corynebacterium* producing a purine nucleotide and a method for producing a purine nucleotide using the same.

8 Claims, No Drawings
Specification includes a Sequence Listing.

MICROORGANISM OF THE GENUS *CORYNEBACTERIUM* PRODUCING PURINE NUCLEOTIDE AND A METHOD FOR PRODUCING PURINE NUCLEOTIDE BY USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187 470USPC SEQUENCE LISTING.txt. The text file is 4.4 KB, was created on Jun. 29, 2020, and is being submitted electronically via EFS-Web.

TECHNICAL FIELD

The present disclosure relates to a microorganism of the genus *Corynebacterium* and a method for producing a purine nucleotide using the same.

BACKGROUND ART

Purine nucleotides, such as 5'-inosine monophosphate (hereinafter, IMP), 5'-xanthosine monophosphate (hereinafter, XMP), 5'-guanosine monophosphate (hereinafter, GMP), 5'-adenylic acid (hereinafter, AMP), etc., are intermediates of the metabolic system of nucleic acid biosynthesis. These intermediates play a physiologically important role in vivo and are widely used in food, medicine, etc. Among them, IMP with a beef flavor and GMP with a mushroom flavor are widely used as food seasoning additives. In addition, it has been known that when these two materials are mixed with monosodium glutamate (MSG), their flavors are further enhanced, and thus, a complex composite seasoning in which these three materials are combined is widely used.

Meanwhile, examples of the method for producing a purine nucleotide may include: (1) a method by enzymatic degradation of ribonucleic acid (RNA) extracted from yeast cells; (2) a method of preparation by fermentation by culturing a microorganism producing a purine nucleotide and directly recovering the purine nucleotide in the cultured liquid; (3) a method by chemical phosphorylation of the nucleoside produced by fermentation; and (4) a method by enzymatic phosphorylation of the nucleoside produced by fermentation, etc. (KR Patent No. 10-1049023, JP Patent Publication No. 4363042, KR Patent No. 10-1210704, and *Agri. Biol. Chem.*, 36(9), 1511-1522). Among them, while Method (1) has problems in terms of supply/demand of raw materials and economic efficiency, Method (2) is widely used due to its economic and environmental advantages. Meanwhile, in the case of the production of GMP (one of purine nucleotides), there is a disadvantage in that the yield is low due to the problem of its cell membrane permeability, and thus, a method of GMP production by enzymatic conversion of XMP produced through microbial fermentation is also utilized.

However, during the purine nucleotide production by fermentation using a microorganism, the microorganism may undergo stress due to temperature, pH, osmotic pressure, malnutrition, and oxidative factors. Among them, particularly in the oxidative stress, reactive oxygen species (ROS), which is an inevitable factor generated during the fermentative production, becomes the main cause, and the ROS may cause abnormal growth of the microorganism.

DISCLOSURE

Technical Problem

The present inventors have studied and made efforts to improve the productivity of purine nucleotides by overcoming oxidative stress that may occur during the fermentation process of a microorganism. As a result, they have confirmed that, in a microorganism where a particular protein is inactivated, the productivity of purine nucleotides is improved as well as the growth of the microorganism is maintained, thereby completing the present disclosure.

Technical Solution

An object of the present disclosure is to provide a microorganism of the genus *Corynebacterium* producing a purine nucleotide, in which a protein consisting of an amino acid sequence of SEQ ID NO: 1 is inactivated.

Another object of the present disclosure is to provide a method for producing a purine nucleotide using the microorganism.

Still another object of the present disclosure is to provide a method for increasing the production of a purine nucleotide in a microorganism of the genus *Corynebacterium*, which includes inactivating a protein of the present disclosure in the microorganism of the genus *Corynebacterium*.

Still another object of the present disclosure is to provide a use of the microorganism for producing a purine nucleotide.

Advantageous Effects

The microorganism producing purine nucleotides of the present disclosure can produce purine nucleotides with high efficiency. Additionally, the prepared purine nucleotides can be applied not only to animal feed or animal feed additives, but also to various products (e.g., human food or food additives, seasonings, pharmaceuticals, etc.).

BEST MODE FOR CARRYING OUT THE INVENTION

The present disclosure is described in detail as follows. Meanwhile, respective descriptions and embodiments disclosed in the present disclosure may also be applied to other descriptions and embodiments. That is, all combinations of various elements disclosed herein fall within the scope of the present disclosure. Further, the scope of the present disclosure is not limited by the specific description below.

To achieve the above objects, an aspect of the present disclosure provides a microorganism of the genus *Corynebacterium* producing a purine nucleotide, in which a protein consisting of an amino acid sequence of SEQ ID NO: 1 is inactivated.

In a specific embodiment, *Corynebacterium stationis* producing a purine nucleotide, in which a protein consisting of an amino acid sequence of SEQ ID NO: 1 is inactivated, is provided.

As used herein, the term "purine nucleotide" collectively refers to a compound, which has a purine nucleoside and in which a phosphate group is bound to a sugar moiety of the nucleoside by an ester bond.

Specifically, the purine nucleotide may be at least one purine nucleotide selected from the group consisting of IMP, XMP, GMP, and AMP, but Purine nucleotides capable of increasing productivity by inactivating a protein consisting of the amino acid sequence of SEQ ID NO: 1 can also be included without limitation.

As used herein, the term, "protein consisting of an amino acid sequence of SEQ ID NO: 1" refers to a protein encoded by a gene of the WhiB-family group, and specifically, it may be a transcriptional regulator WhiB. The protein includes four conserved cysteine residues that form an oxygen and nitrogen oxides-sensitive cluster (4Fe-4S) and the protein is known to play an important role in exhibiting various biological properties of Actinomycetes. Its functions identified to date are known to be its involvement in overall cellular functions (e.g., pathogenesis, antibiotic resistance, cell growth, etc.), but their detailed functions and mechanisms have not been well studied.

The protein having an amino acid sequence of SEQ ID NO: 1 of the present disclosure may be a protein including an amino acid sequence of SEQ ID NO: 1, a protein essentially consisting of an amino acid sequence of SEQ ID NO: 1, or a protein consisting of an amino acid sequence of SEQ ID NO: 1, but the protein is not limited thereto.

Additionally, the protein of the present disclosure may be a protein consisting of an amino acid sequence described as SEQ ID NO: 1, but any sequence having an activity identical to the protein can be included without limitation, and one of ordinary skill in the art can obtain sequence information from known databases (e.g., GenBank of the NCBI, etc.). Additionally, the protein having an amino acid sequence of SEQ ID NO: 1 of the present disclosure may be a protein including an amino acid sequence of SEQ ID NO: 1, or a protein including an amino acid sequence having a homology or identity to the amino acid sequence of SEQ ID NO: 1 of at least 60%, 70%, 80%, 83%, 84%, 85%, 86%, 87%, 88%, 89%, 90%, 91%, 92%, 93%, 94%, 95%, 97%, 98%, or 99%. Additionally, it is apparent that any protein having an amino acid sequence with deletion, modification, substitution, or addition in part of the sequence can also belong to the scope of the present disclosure, as long as the protein has an amino acid sequence with any of the above homologies or identities and exhibits a biological activity corresponding to the above protein.

Furthermore, any polypeptide, which is encoded by a polynucleotide hybridized under stringent conditions with a probe that can be prepared from known gene sequences (e.g., sequences complementary to all or part of a nucleotide sequence encoding the polypeptide constituting above protein) and has an activity identical to the protein consisting of an amino acid sequence of SEQ ID NO: 1, can be included without limitation.

That is, in the present disclosure, although it is described as "a protein or polypeptide including an amino acid sequence of a particular SEQ ID NO", "a protein or polypeptide consisting of an amino acid sequence of a particular SEQ ID NO", or "a protein or polypeptide having an amino acid sequence of a particular SEQ ID NO", it is apparent that any protein which has an amino acid sequence with deletion, modification, substitution, conservative substitution or addition in part of the sequence can also be included within the scope of the present disclosure, as long as the protein has an activity identical or corresponding to the polypeptide consisting of an amino acid sequence of the particular SEQ ID NO.: for example, a case where a sequence that does not change the function of the protein is added to the N-terminus and/or C-terminus of the amino acid sequence, a case where the amino acid sequence has a naturally occurring mutation, or a case where the amino acid sequence has a silent mutation or conservative substitution thereof.

The term "conservative substitution" refers to a substitution of one amino acid with another amino acid having similar structural and/or chemical properties. Such an amino acid substitution may generally occur based on similarities in polarity, charge, solubility, hydrophobicity, hydrophilicity, and/or amphipathic nature of residues. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

As used herein, the term "polynucleotide" has a meaning that generally encompasses a DNA or RNA molecule, and a nucleotide (i.e., the basic structural unit of a polynucleotide) can include not only natural nucleotides, but also its analogs in which the sugar or base moiety is modified (see Scheit, Nucleotide Analogs, John Wiley, New York (1980); Uhlman and Peyman, *Chemical Reviews,* 90:543-584 (1990)).

The polynucleotide sequence of a gene encoding the protein having the amino acid sequence of SEQ ID NO: 1 can be obtained from a known database (e.g., GenBank of the NCBI, etc.), but is not limited thereto.

The polynucleotide may be a polynucleotide encoding the protein having the amino acid sequence of SEQ ID NO: 1 of the present disclosure, or a polynucleotide encoding the protein having a homology or identity to the protein of the present disclosure of 60%, 70%, 80%, 83%, 84%, 85%, 86%, 87%, 88%, 89%, 90%, 91%, 92%, 93%, 94%, 95%, 97%, 98%, or 99%.

Specifically, the protein having the amino acid sequence of SEQ ID NO: 1 may be a polynucleotide having a homology or identity to the polynucleotide sequence of SEQ ID NO: 2 of at least 80%, 85%, 90%, 95%, 96%, 97%, 98%, 99%, or 100%. However, it is apparent that any polynucleotide sequence, which encodes the protein having an activity corresponding to the protein consisting of the amino acid sequence of SEQ ID NO: 1, can be included in the scope of the present disclosure, without being limited thereto.

Additionally, it is apparent that, based on the genetic code degeneracy, any polynucleotide which can be translated into a protein consisting of the same amino acid sequence or a protein having a homology thereto can also be included in the scope of the present disclosure. Additionally, the nucleotide sequence may be any sequence capable of hybridizing with a probe, which can be prepared from a known gene sequence (e.g., a sequence complementary to all or part of the above nucleotide sequences), under stringent conditions to encode a protein having the activity of the protein consisting of the amino acid sequence of SEQ ID NO: 1.

The term "stringent conditions" refers to conditions which enables specific hybridization between polynucleotides. Such conditions are specifically described in a literature (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). The conditions may include performing hybridization between genes having a high homology or identity, for example, a homology or identity of 40% or higher, specifically 70% or higher, 80% or higher, 85% or higher, and 90% or higher, more specifically 95% or higher, even more specifically 97% or higher, and most specifically 99% or higher, while not performing hybridization between genes having a homology or identity of lower than the above homologies or identities; or performing conventional washing conditions for southern hybridization, i.e., washing once, specifically, twice or three times at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS. Hybridization requires that two nucleic acids have a complementary sequence(s), although there may be a mismatch(es) between bases depending on the stringency of the hybridization. The term "complementary" is used to describe the relationship between nucleotide bases that can hybridize with each other. For example, with respect to DNA, adenosine is complementary to thymine while cytosine is complementary to guanine. Accordingly, the present disclosure may also include isolated nucleic acid fragments complementary to the entire sequence as well as substantially similar nucleic acid sequences.

Specifically, polynucleotides having a homology or identity can be detected at a $T_m$ value of 55° C. using hybridization conditions that include a hybridization step and using the conditions described above. Additionally, the $T_m$ value may be 60° C., 63° C., or 65° C., but the temperature is not limited thereto and may be appropriately adjusted by those skilled in the art according to the purpose.

The stringency suitable for the hybridization of polynucleotides depends on the length and degree of complementarity of the polynucleotides, and the variables are well known in the art (see Sambrook et al., supra, 9.50 to 9.51 and 11.7 to 11.8).

As used herein, the term "homology" or "identity" refers to a degree of identity between two given amino acid sequences or nucleotide sequences, and they may be expressed as a percentage. These terms "homology" and "identity" may often be used interchangeably. In the present specification, a homologous sequence having an activity identical or similar to a given amino acid sequence or polynucleotide sequence is represented as "% homology".

Sequence homology or identity of conserved polynucleotides or polypeptides is determined by standard alignment algorithm, and default gap penalties established by a program being used may be used together. Actually, homologous or identical sequences may hybridize to each other along the entire sequence or at least about 50%, 60%, 70%, 80%, or 90% or more of the entire length under moderate or highly stringent conditions. In hybridization, polynucleotides including a degenerate codon(s) instead of a codon(s) are also considered.

Whether any two polynucleotide- or polypeptide sequences have a homology, similarity, or identity can be determined using computer algorithms known in the art (e.g., "FASTA" program using default parameters disclosed by Pearson et al. (1988) [*Proc. Natl. Acad. Sci. USA* 85: 2444]). Alternatively, Needleman-Wunsch algorithm (1970, *J. Mol. Biol.* 48: 443-453) performed in a Needleman program of The European Molecular Biology Open Software Suite of EMBOSS package (Rice et al., 2000, Trends Genet. 16: 276-277) (version 5.0.0 or a later version) may be used to determine the same (including GCG program package (Devereux, J., et al., *Nucleic Acids Research* 12: 387 (1984)), BLASTP, BLASTN, FASTA (Atschul, [S.] [F.,] [ET AL., *J Molec Biol* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, homology, similarity, or identity may be determined using BLAST from the National Center for Biotechnology Information database or ClustalW.

The homology, similarity, or identity between polynucleotides or polypeptides, for example, may be determined by comparing the given sequence information using the GAP computer program, such as a program introduced by Needleman et al. (*J Mol Biol.* 48: 443 (1970)) as disclosed by Smith and Waterman (*Adv. Appl. Math* (1981) 2: 482). In brief, the GAP program defines homology, similarity, or identity as the number of similar aligned symbols (i.e., nucleotides or amino acids) divided by the total number of the symbols in a shorter of the two sequences. The default parameters for the GAP program may include: (1) a unary comparison matrix (including a value 1 for identity and a value 0 for non-identity) and the weighted comparison matrix of Gribskov, et al., (*Nucl. Acids Res.* 14: 6745 (1986)) as described by Schwartz and Dayhoff, eds. (Atlas Of Protein Sequence And Structure, National Biomedical Research Foundation, pp. 353-358 (1979) or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps. Therefore, the term "homology" or "identity", as used herein, refers to the relevance between sequences.

In the present disclosure, the microorganism of the genus *Corynebacterium* producing a purine nucleotide may be one in which a protein including the amino acid sequence of SEQ ID NO: 1 is inactivated.

In particular, the inactivation of the protein including the amino acid sequence of SEQ ID NO: 1 may be used interchangeably in the same sense as in the inactivation of the WhiB-family protein, the inactivation of the WhiB transcriptional regulator, or the inactivation of a protein encoded by a gene including the polynucleotide sequence of SEQ ID NO: 2.

As used herein, the term "the protein including the amino acid sequence of SEQ ID NO: 1 is inactivated" means that the protein including the amino acid sequence of SEQ ID NO: 1 is not expressed at all; or the protein may be expressed but it has no or reduced activity, compared to its parent strain or a non-modified strain. Additionally, the above term means that the protein WhcEDBA, which is encoded by a gene of the WhiB-family group, has no activity or its activity is reduced, compared to its parent strain or a non-modified strain. In particular, the reduction described above is a concept which includes a case where the activity of a protein is reduced due to a mutation, deletion, etc. of a gene encoding the protein compared to the activity of the protein originally possessed by a microorganism; a case where the degree of the overall intercellular activity of the protein is lower than that of its native wild-type strain or the strain before modification, due to inhibition of expression of the gene encoding the protein or inhibition of translation of the gene, etc.; and a combination of both cases.

In the present disclosure, it was first confirmed that inactivation of the above protein is related to the productivity of purine nucleotides.

In the present disclosure, the inactivation may be achieved by the application of various methods known in the art. Examples of the methods include: 1) a method of deleting all or part of the gene encoding the protein; 2) a method of modifying the expression control sequence to reduce the expression of the gene encoding the protein; 3) a method of modifying the sequence of the gene encoding the protein so that the activity of the protein is removed or weakened; 4) a method of introducing an antisense oligonucleotide (e.g., antisense RNA), which binds complementarily to a transcript of the gene encoding the protein; 5) a method of making the attachment of a ribosome impossible by forming a secondary structure by adding a sequence, which is complementary to the Shine-Dalgarno (SD) sequence, on a front end of the SD sequence of the gene encoding the protein; 6) a method of reverse transcription engineering (RTE), in which a reversely-transcribed promoter is added to the 3' terminus of the open reading frame (ORF) of the polynucleotide sequence of the gene encoding the protein, etc.; and the inactivation may be achieved by a combination of these methods, but the methods are not particularly limited thereto.

Specifically, the method of deleting all or part of the gene encoding the protein may be performed by replacing the polynucleotide encoding the endogenous target protein within the chromosome with a polynucleotide or marker gene having a partially-deleted nucleotide sequence using a vector for chromosomal insertion in a microorganism. As an example of the method of deleting all or part of a polynucleotide, a method of deleting a polynucleotide by homologous recombination may be used, but the method is not limited thereto.

Additionally, the method of deleting all or part of the gene may be performed such that a mutation is induced in the gene using light (e.g., ultraviolet rays) or chemicals, and strains in which a target gene is deleted are selected from the mutants obtained. The above method of deleting a gene includes a method by DNA recombinant technology. In the DNA recombination technology, for example, there may be a method in which homologous recombination occurs by introducing a nucleotide sequence or vector containing a nucleotide sequence homologous to a target gene into the microorganism.

Additionally, the nucleotide sequence or vector to be introduced may include a dominant selectable marker, but is not limited thereto.

Additionally, the method of modifying an expression control sequence may be achieved by the application of various methods known in the art. As examples of the method, the modification of the expression control sequence may be performed by inducing a mutation in the polynucleotide sequence by deletion, insertion, non-conservative or conservative substitution, or a combination thereof so as to further weaken the activity of the expression control sequence; or by replacing the polynucleotide sequence with a polynucleotide sequence having a weaker activity. The expression control sequence may include a promoter, an operator sequence, a sequence encoding a ribosome-binding site, sequences controlling the termination of transcription and translation, etc., but the expression control sequence is not limited thereto.

Additionally, the method of modifying a gene sequence may be performed by inducing a mutation in the gene sequence by deletion, insertion, non-conservative or conservative substitution, or a combination thereof so as to further weaken the activity of the protein; or by replacing the gene sequence with a gene sequence improved to have a weaker activity or a gene sequence improved to have no activity, but the method of modifying a gene sequence is not limited thereto.

As used herein, the term "microorganism producing a purine nucleotide" or "microorganism having a purine nucleotide-producing ability" refers to a microorganism which naturally has a purine nucleotide-producing ability; or a microorganism in which a purine nucleotide-producing ability, which is not possessed by its parent strain, is provided. Specifically, the microorganism may be one, in which the protein including the amino acid sequence of SEQ ID NO: 1, a WhiB-family protein, or a WhiB transcriptional regulator is inactivated, thus having a purine nucleotide-producing ability.

In the present disclosure, "microorganism of the genus *Corynebacterium*" may include all microorganisms of the genus *Corynebacterium*. Specifically, the microorganism of the genus *Corynebacterium* may be *Corynebacterium stationis*, *Corynebacterium glutamicum*, *Corynebacterium phocae*, *Corynebacterium flavescens*, *Corynebacterium humireducens*, *Corynebacterium halotolerans*, *Corynebacterium pollutisoli*, *Corynebacterium marinum*, *Corynebacterium freiburgense*, *Corynebacterium cystitidis*, *Corynebacterium durum*, *Corynebacterium pilosum*, or *Corynebacterium testudinoris*, and more specifically *Corynebacterium stationis*, but the microorganism is not limited thereto.

Meanwhile, although it has been already known that a microorganism of the genus *Corynebacterium* can produce purine nucleotides, the microorganism has a significantly low nucleotide-producing ability and the gene acting on its production mechanism or the principle of the mechanism has not been known. Accordingly, the microorganism of the genus *Corynebacterium* producing a purine nucleotide of the present disclosure refers to a wild-type microorganism of the genus *Corynebacterium* itself; a microorganism of the genus *Corynebacterium* in which the activity of the gene associated with the mechanism of purine nucleotide production is enhanced or inactivated, thus having an improved purine nucleotide-producing ability; or a microorganism of the genus *Corynebacterium* in which the activity of an exogenous gene is introduced or enhanced, thus having an improved purine nucleotide-producing ability. Specifically, the microorganism of the genus *Corynebacterium* may be *Corynebacterium stationis* in which the biosynthetic pathway of purine nucleotides is enhanced, and the enhancement may mean that the activity of a protein involved in the biosynthetic pathway is enhanced. Alternatively, the microorganism of the genus *Corynebacterium* may be *Corynebacterium stationis* in which the activity of a protein involved in the degradation pathway of purine nucleotides or their precursor(s) is inactivated.

In particular, in the case where the purine nucleotide is 5'-inosine monophosphate (IMP), examples of the protein involved in the biosynthetic pathway of purine nucleotides may include at least one protein selected from the group consisting of amidophosphoribosyltransferase (PurF), phosphoribosylamine-glycine ligase (PurD), phosphoribosylglycinamide formyltransferase (PurN), phosphoribosylformylglycinamidine synthase (PurL), AIR synthetase (FGAM cyclase), phosphoribosylaminoimidazole carboxylase, phosphoribosylaminoimidazolesuccinocarboxamide synthase, adenylosuccinate lyase (ADSL), phosphoribosylaminoimidazolecarboxamide formyltransferase, and inosine monophosphate synthase.

Additionally, in the case where the purine nucleotide is 5'-xanthosine monophosphate (XMP), examples of the protein in which the activity is enhanced may further include IMP dehydrogenase, in addition to the group consisting of the above proteins.

Additionally, in the case where the purine nucleotide is 5'-guanosine monophosphate (GMP), examples of the protein in which the activity is enhanced may further include IMP dehydrogenase and/or GMP synthase, in addition to the group consisting of the above proteins.

Additionally, in the case where the purine nucleotide is 5'-adenylic acid (AMP), examples of the protein in which the activity is enhanced may further include adenylosuccinate synthase (purA), in addition to the group consisting of the above proteins.

Most specifically, the protein involved in the biosynthetic pathway of purine nucleotides may be amidophosphoribosyltransferase (PurF), but the protein is not limited thereto.

Another aspect of the present disclosure provides a method for producing purine nucleotides, which includes a step of culturing the above microorganism according to the present disclosure in a medium.

The above production method may further include a step of recovering purine nucleotides.

The microorganism and purine nucleotides are as described above.

As used herein, the term "culture" means that a microorganism is grown under appropriately and artificially controlled environmental conditions. In the present disclosure, the culture process of a microorganism of the genus *Corynebacterium* may be performed using the methods widely known in the art. Specifically, the culture may be performed continuously in a batch process, fed batch process, or repeated fed batch process, but the culture process is not limited thereto.

The step of culturing the microorganism may be performed in batch culture, continuous culture, fed batch culture, etc. known in the art, but the step of culturing the microorganism is not particularly limited thereto. The medium and other culture conditions used for culturing the microorganism of the present disclosure are not particularly limited, but any medium used in the conventional culture for a microorganism may be used. Specifically, the microorganism of the present disclosure may be cultured under aerobic conditions in a conventional medium containing an appropriate carbon source, nitrogen source, phosphorus source, inorganic compound, amino acid, and/or vitamin, etc. while adjusting temperature, pH, etc. The medium for culturing a *Corynebacterium* strain is known (e.g., Manual of Methods for General Bacteriology by the American Society for Bacteriology, Washington D.C., USA, 1981).

The carbon sources that can be used in the medium include saccharides and carbohydrates (e.g., glucose, saccharose, lactose, fructose, maltose, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), organic acids (e.g., acetic acid), etc. These materials may be used alone or as a mixture, but are not limited thereto.

The nitrogen sources that can be used in the medium include peptone, yeast extract, meat gravy, malt extract, corn steep liquor, bean flour, and urea, or an inorganic compound (e.g., ammonium sulfate, ammonium chloride, ammonium phosphate, ammonium carbonate, and ammonium nitrate), etc. The nitrogen sources may also be used alone or as a mixture, but are not limited thereto.

The phosphorous sources that can be used in the medium may include potassium dihydrogen phosphate, dipotassium hydrogen phosphate, and sodium-containing salts corresponding thereto. Additionally, the culture medium may include a metal salt (e.g., magnesium sulfate or iron sulfate) required for growth. Finally, the culture medium may include essential growth materials (e.g., amino acids and vitamins), in addition to the above materials. Additionally, precursors suitable for a culture medium may be used. The above raw materials may be added in a batch culture mode or continuous culture mode during a culture process by a method suitable for a cultured medium.

The pH of a cultured medium may be adjusted during the culture of the microorganism using a base compound (e.g., sodium hydroxide, potassium hydroxide, and ammonia) or an acid compound (e.g., phosphoric acid or sulfuric acid) in an appropriate manner. Additionally, foam generation can be prevented using an antifoaming agent (e.g., fatty acid polyglycol ester). Additionally, oxygen or oxygen-containing gas (e.g., air) may be injected into the cultured medium in order to maintain an aerobic state of the cultured medium. The temperature of the cultured medium may normally be maintained at 20° C. to 45° C., and specifically 25° C. to 40° C. The culture process may be continued until the desired amount of L-amino acid production is obtained, and specifically, for 10 to 160 hours.

The purine nucleotides produced by the above culture process may be released into the medium or remain in the cells.

The method for producing purine nucleotides of the present disclosure, after the step of culture, may further include a step of recovering purine nucleotides from the microorganism or the medium.

The recovery of the purine nucleotides may be performed by a conventional method known in the art. As the method for recovery, centrifugation, filtration, anion-exchange chromatography, crystallization, etc. may be used. For example, the cultured medium may be centrifuged at a low speed to remove biomass and the obtained supernatant may be separated through ion exchange chromatography, but the method for recovery is not limited thereto, and the desired purine nucleotides may be recovered from the cultured microorganism or the medium by an appropriate method known in the art.

The recovery step may further include a separation process and/or a purification process.

Still another aspect of the present disclosure provides a use of a microorganism of the genus *Corynebacterium*, in which a protein including the amino acid sequence of SEQ ID NO: 1 is inactivated, for the increase of purine nucleotide production Still another aspect of the present disclosure provides a method for increasing the production of purine nucleotides, which includes a step of inactivating the protein that includes the amino acid sequence of SEQ ID NO: 1 of the present disclosure in a microorganism of the genus *Corynebacterium*.

The terms "purine nucleotide", "a protein including the amino acid sequence of SEQ ID NO: 1", "inactivation" and "a microorganism of the genus *Corynebacterium*" are as described above.

DETAILED DESCRIPTION OF THE INVENTION

Hereinafter, the present disclosure will be described in detail through exemplary embodiments. However, these exemplary embodiments are for illustrative purposes only and are not intended to limit the scope of the present disclosure.

Example 1: Preparation of Recombinant Vector for the Purpose of Inactivation of WhiB-Family Protein A WhiB family protein was selected as a target protein to be inactivated for the increase of a purine nucleotide-producing ability.

Example 1-1: Selection of WhiB Family Protein of *Corynebacterium stationis*

A WhiB family protein was screened from the genome of a wild-type *Corynebacterium stationis* ATCC 6872 strain, and among the genes in the genome, one kind of gene which is considered to be involved in purine nucleotide production was selected. Based on the nucleotide sequences reported to the NIH Genbank (USA), the gene was confirmed that it is a transcriptional regulator, WhiB.

Example 1-2: Preparation of Protein-Encoding Gene Fragment for Inactivation of WhiB Family Protein Chromosomal genes of the ATCC 6872 strain, which is a wild-type strain of *Corynebacterium stationis*, were extracted using the G-spin total DNA extraction kit (Intron, Cat. No 17045). Then, polymerase chain reaction (PCR) was performed using the chromosomal genes as a template.

Then, for the inactivation of a WhiB family protein, the endogenous activities of these proteins were completely removed by deleting the genes encoding these proteins; or the expression levels of these proteins were minimized by weakening the genes encoding these proteins.

Specifically, the endogenous activities of the above genes were removed using the vector prepared according to Example 1-2-1, and each of the endogenous initiation codon (i.e., ATG) of the above strain was substituted with GTG or TTG using the vector prepared according to Example 1-2-2. It is known that the GTG or TTG codon has a lower efficiency of protein expression compared to the ATG codon.

Example 1-2-1: Preparation of Vector for Deletion of the Gene Encoding WhiB Family Protein In order to prepare a vector for the purpose of deletion of a gene encoding a WhiB family protein, each of the gene fragments (deletion-A and deletion-B) was obtained by performing PCR using the genomic DNA of ATCC 6872 strain as a template along with a primer pair of SEQ ID NO: 3 and SEQ ID NO: 4 and a primer pair of SEQ ID NO: 5 and SEQ ID NO: 6, respectively. In particular, PCR was performed under the following conditions: denaturation at 94° C. for 5 minutes; 25 cycles of denaturation at 94° C. for 30 seconds, annealing at 55° C. for 30 seconds, and polymerization at 72° C. for 2 minutes; and polymerization at 72° C. for 7 minutes.

As a result, two polynucleotide fragments (i.e., a 1,026 bp deletion-A fragment and a 1,044 bp deletion-B fragment) could be obtained. An overlapping PCR was performed using these two fragments as templates along with primers of SEQ ID NO: 3 and SEQ ID NO: 6, and thereby, a 2,050 bp PCR product (hereinafter, named as "deletion fragment") was obtained.

The obtained deletion fragment was treated with a restriction enzyme XbaI (New England Biolabs, Beverly, Mass., USA) and ligated to pDZvector, which was treated with the same restriction enzyme, using T4 ligase (New England Biolabs, Beverly, Mass., USA). The prepared gene was transformed into *E. coli* DH5a, and the transformants were selected in an LB medium containing kanamycin, and then DNA was obtained using the DNA-spin plasmid total DNA kit (iNtRON).

The vector prepared by the above method, which aims to delete the gene encoding a WhiB family protein, was named as "pDZ-deletion".

Example 1-2-2: Preparation of Vector for Reducing the Expression of WhiB-Family Protein In order to prepare a vector aiming to weaken the gene encoding a WhiB family protein, the initiation codon of the ATCC 6872 strain (i.e., ATG) was modified to TTG or GTG.

First, in order to prepare a strain in which the initiation codon is modified to TTG, each of the gene fragments (alt-A and alt-B where the initiation codon is modified to TTG or GTG) was obtained by performing PCR using the genomic DNA of ATCC 6872 strain as a template along with a primer pair of SEQ ID NO: 7 and SEQ ID NO: 8 and a primer pair of SEQ ID NO: 9 and SEQ ID NO: 10, respectively. As a result, two polynucleotides (i.e., a 974 bp alt-A fragment and a 982 bp alt-B fragment) could be obtained. An overlapping PCR was performed using these two fragments as templates along with primers of SEQ ID NO: 7 and SEQ ID NO: 10, and thereby, a 1,955 bp PCR product (hereinafter, named as "alt fragment") was obtained.

Additionally, in order to prepare a strain in which the initiation codon is modified to GTG, each of the gene fragments (alt-A and alt-B) was obtained by performing PCR using the genomic DNA of ATCC 6872 strain as a template along with a primer pair of SEQ ID NO: 7 and SEQ ID NO: 11 and a primer pair of SEQ ID NO: 12 and SEQ ID NO: 10, respectively. As a result, two polynucleotides (i.e., a 974 bp alt-A fragment and a 982 bp alt-B fragment) could be obtained. An overlapping PCR was performed using these two fragments as templates along with primers of SEQ ID NO: 7 and SEQ ID NO: 10, and thereby, a 1,955 bp PCR product (hereinafter, named as "alg fragment") was obtained.

Meanwhile, the conditions for each PCR are the same as follows: denaturation at 94° C. for 5 minutes; 25 cycles of denaturation at 94° C. for 30 seconds, annealing at 55° C. for 30 seconds, and polymerization at 72° C. for 2 minutes; and polymerization at 72° C. for 7 minutes.

The obtained gene fragments were each treated with a restriction enzyme XbaI (New England Biolabs, Beverly, Mass., USA) and ligated to pDZvector, which was treated with the same restriction enzyme, using T4 ligase (New England Biolabs, Beverly, Mass., USA). Each of the prepared gene was transformed into *E. coli* DH5a, and the transformants were selected in an LB medium containing kanamycin, and then DNA was obtained using the DNA-spin plasmid total DNA kit (iNtRON).

The vectors prepared by the above method, which aim to weaken the gene encoding a WhiB family protein, were named as "pDZ-alt" and "pDZ-alg", respectively.

Meanwhile, the sequences of primers used for the preparation of the vectors are shown in Table 1 below.

TABLE 1

| | |
|---|---|
| SEQ ID NO: 3 | TGCTCTAGA GATCTAGCAC GCCTAAAGAGTCG |
| SEQ ID NO: 4 | GTAGGTGTCCGCCTGAGTTG |
| SEQ ID NO: 5 | CAACTCAGGCGGACACCTACTC ACTAACTGGGCTGATTATCTCG |
| SEQ ID NO: 6 | TGCTCTAGAGGTGCCCTTCATC ATCAGGT |
| SEQ ID NO: 7 | CGC GGA TCC CAGCCATTAG GTAAGGTGCTTG |

TABLE 1-continued

| | |
|---|---|
| SEQ ID NO: 8 | AGAGGCGTATTCACGCTCTG |
| SEQ ID NO: 9 | CAGAGCGTGAATACGCCTCTTGAGATTATGTGTGGATAAGCAGAAG |
| SEQ ID NO: 10 | CGC GGA TCC CGAGGATACAAAGCCCACGA |
| SEQ ID NO: 11 | CGAGGCGTATTCACGCTCTG |
| SEQ ID NO: 12 | CAGAGCGTGAATACGCCTCGTGAGATTATGTGTGGATAAGCAGAAG |

Example 2: Preparation of Strain, in which WhiB Family Protein is Inactivated, Using Wild-Type Strain Producing Purine Nucleotides and Evaluation of Purine Nucleotide-Producing Ability of the Same

Example 2-1: Preparation of Strain, in which WhiB Family Protein is Inactivated, Using Wild-Type Derived Strain Producing XMP Among Purine Nucleotides The two kinds of vectors (i.e., pDZ-alt and pDZ-alg) prepared according to Example 1 were each individually transformed into the *Corynebacterium stationis* KCCM-10530 strain (KR Patent No. 10-0542568) by electroporation, and the colonies grown in a selection medium containing kanamycin (25 mg/L) were first selected.

Then, strains, in which the gene encoding a WhiB family protein is deleted or the initiation codon is modified to a weakened form (i.e., ATG→TTG or ATG→GTG), were obtained through a secondary cross-over process using a homology between the endogenous gene of the strains and the polynucleotides included in the vectors above.

Meanwhile, the strain in which the gene encoding the WhiB family protein is deleted was selected using the primers of SEQ ID NO: 13 and SEQ ID NO: 6. When PCR is performed using the above primers, the wild-type strain produced a 1,680 bp fragment, whereas in the strain where the gene is deleted, a 1,414 bp fragment was detected.

Additionally, the strain in which the gene encoding the WhiB family protein is weakened was selected based on mismatch PCR. The 'ATG→TTG' mutation was selected using the primers of SEQ ID NO: 14 and SEQ ID NO: 6, whereas the 'ATG→GTG' mutation was selected using SEQ ID NO: 15 and SEQ ID NO: 6. Since SEQ ID NO: 14 and SEQ ID NO: 15 each includes T or G at 3' terminus instead of A, which is a nucleotide sequence of the wild-type strain, PCR fragments were allowed to be detected only when there was a mutation. The strains which were confirmed first by mismatch PCR were finally confirmed through sequence analysis of the gene.

Finally, the strains obtained by the above method were named as follows: the strain in which the gene encoding the WhiB family protein is deleted was named as "CN02-1545"; the strain in which the above gene is weakened due to the substitution of the initiation codon to a TTG form was named as "CJX-1546"; and the strain in which the above gene is weakened due to the substitution of the initiation codon to a GTG form was named as "CJX-1547".

Meanwhile, the sequences of primers used for the preparation of the strains are shown in Table 2 below.

TABLE 2

| | |
|---|---|
| SEQ ID NO: 13 | CATGTTGTTGCCCTCGGAATC |
| SEQ ID NO: 14 | CGTGAATACGCCTCT |
| SEQ ID NO: 15 | CGTGAATACGCCTCG |

Meanwhile, the CNO2-1545 strain was internationally deposited at the Korean Culture Center of Microorganisms (KCCM) on Nov. 7, 2017, under the provisions of the Budapest Treaty and assigned Accession Number KCCM12152P.

Example 2-2: Evaluation of XMP-Producing Ability of Strain in which WhiB Family Protein is Inactivated In order to measure the XMP-producing ability of the *Corynebacterium stationis* KCCM-10530 strain, which produces XMP among purine nucleotides, and CNO2-1545, CJX-1546, and CJX-1547 strains prepared in Example 2-1, the culture method described below was used.

The seed medium below (5 mL) was dispensed into each test tube (diameter: 18 mm), which was autoclaved according to the conventional method, inoculated with a strain to be used, and cultured with shaking at 30° C. at 180 rpm for 18 hours. The resultant was used as a seed culture solution. Among the fermentation media, the main medium and an additional sterile medium were each autoclaved according to the conventional method, and dispensed into a 500 mL Erlenmeyer flask for shaking, which was autoclaved in advance, in an amount of 29 mL and 10 mL, respectively, phagocytized with the seed culture solution (1 mL) and cultured for 72 hours. The revolution rate was set at 200 rpm and the temperature was adjusted to 30° C.

The medium compositions used are as follows. The amount of XMP production was measured by a method using HPLC after completion of culture, and the results are shown in Table 3 below. The concentration of XMP accumulation was indicated as "5'-sodium xanthylate.$7H_2O$".

XMP Flask Seed Medium

Glucose 30 g/L, Peptone 15 g/L, Yeast extract 15 g/L, NaCl 2.5 g/L, Urea 3 g/L, Adenine 150 mg/L, Guanine 150 mg/L, pH 7.2

XMP Flask Production Medium (Main Medium)

Glucose 60 g/L, Magnesium sulfate 10 g/L, Calcium chloride 10 mg/L, Iron sulfate 20 mg/L, Manganese sulfate 10 mg/L, Zinc sulfate 10 mg/L, Copper sulfate 1 mg/L, Biotin 100 μg/L, Thiamine 5 mg/L, Adenine 30 mg/L, Guanine 30 mg/L, pH 7.2

XMP Flask Production Medium (Additional Sterile Medium)

Potassium dihydrogen phosphate 10 g/L, Dipotassium hydrogen phosphate 10 g/L, Urea 7 g/L, Ammonium sulfate 5 g/L

TABLE 3

| Strain No. | XMP (g/L) | Productivity (g/L/hr) |
|---|---|---|
| KCCM10530 | 11.8 | 0.148 |
| CN02-1545 | 13.1 | 0.191 |
| CJX-1546 | 12.3 | 0.188 |
| CJX-1547 | 12.5 | 0.198 |

In particular, in Table 3, the productivity represents the amount of XMP produced per unit hour at the time-point of 48 hours after completion of culture.

As shown in Table 3, it was confirmed that the parent strain (i.e., KCCM10530 strain) produced XMP at a concentration of 11.8 g/L after completion of flask culture; the CNO2-1545 strain showed an increase in the amount of XMP production by 1.3 g/L; the CJX-1546 strain showed an increase in the amount of XMP production by 0.5 g/L; and the CJX-1547 strain showed an increase in the amount of XMP production by 0.7 g/L. These results confirmed that the amount of XMP production of the above strains was improved by 11%, 4%, and 6%, respectively, compared to that of the parent strain.

Additionally, while the parent strain (i.e., KCCM10530 strain) showed a productivity of 0.148 g/L/hr, the CNO2-1545 strain showed a productivity of 0.191 g/L/hr, the CJX-1546 strain showed a productivity of 0.188 g/L/hr, and the CJX-1547 strain showed a productivity of 0.198 g/L/hr. These results confirmed that the XMP productivity of the above strains was improved by 29%, 27%, and 34%, respectively, compared to that of the parent strain.

The above results imply that when the WhiB family protein of the present disclosure is inactivated in a strain, its purine nucleotide production is increased.

Example 3: Preparation of Strain, in which WhiB Family Protein is Inactivated, Using Purine Nucleotide-Producing Mutant Strain, in which Gene of Purine Biosynthetic Pathway is Enhanced, and Evaluation of Purine Nucleotide-Producing Ability of the Same

Example 3-1: Preparation of Strain, in which WhiB Family Protein is Inactivated, Using Mutant Strain Producing XMP Among Purine Nucleotides A strain, in which a gene encoding a WhiB family protein is inactivated, was prepared using an XMP-producing strain, in which a gene of the purine biosynthetic pathway is enhanced. Specifically, the XMP-producing strain, in which a gene of the purine biosynthetic pathway is enhanced, being a modified strain of KCCM-10530 where PurF is enhanced, is a strain in which the initiation codon of purF gene (i.e., GTG) is converted to ATG. The KCCM-10530 strain, in which the gene of the purine biosynthetic pathway, purF, is enhanced, was named as CJX-1544 [KCCM-10530_purF (g1a)]. The CJX-1544 [KCCM-10530_purF (g1a)] strain was transformed with the pDZ-deletion vector, which is a recombinant vector prepared in Example 1, by electroporation. The colonies grown in a selection medium containing kanamycin (25 mg/L) were first selected.

Then, a strain in which a gene encoding the WhiB family protein is deleted was obtained through a secondary cross-over process using a homology between the endogenous gene of the above strain and the polynucleotide included in the above vector. Meanwhile, the strain in which a gene encoding the WhiB family protein is deleted was obtained in the same manner as in Example 2 using the primers of SEQ ID NO: 13 and SEQ ID NO: 6.

Finally, the strain, in which a gene encoding the WhiB family protein is deleted, obtained by the above method, was named as "CJX-1553".

Example 3-2: Evaluation of the Ability of Producing XMP Among Purine Nucleotides of Strain in which Gene Encoding WhiB Family Protein is Inactivated In order to measure the XMP-producing abilities of the CJX-1544 strain, in which the gene of the purine biosynthetic pathway (i.e., purF) is enhanced, and the CJX-1553 strain prepared in Example 3-1, the culture method as in Example 2-2 was used. After completion of culture, the amount of XMP production in each strain was measured by a method using HPLC, and the results are shown in Table 4 below.

TABLE 4

| Strain No. | XMP (g/L) | Productivity (g/L/hr) |
|---|---|---|
| CJX-1544 | 14.0 | 0.183 |
| CJX-1553 | 15.5 | 0.212 |

In particular, in Table 4, the productivity represents the amount of XMP produced per unit hour at the time-point of 48 hours after completion of culture.

As shown in Table 4, it was confirmed that the amount of XMP production was increased in the CJX-1553 strain by 1.5 g/L compared to its parent strain (i.e., CJX-1544) in which a purine biosynthetic pathway factor (i.e., purF) is enhanced. The above result confirmed that the amount of XMP production in the CJX-1553 strain was improved by 10.7% compared to that of its parent strain (i.e., CJX-1544).

Additionally, it was confirmed that the parent strain (i.e., CJX-1544) showed a productivity of 0.183 g/L/hr and the CJX-1553 strain showed a productivity of 0.212 g/L/hr. The above result confirmed that the XMP productivity of the CJX-1553 strain is improved by 16% compared to its parent strain (i.e., CJX-1544).

Example 4: Preparation of Strain, in which WhiB Family Protein is Inactivated, Using Purine Nucleotide-Producing Wild-Type Strain, and Evaluation of Purine Nucleotide-Producing Ability of the Same

Example 4-1: Preparation of Strain, in which WhiB Family Protein is Inactivated, Using Wild-Type Derived Strain Producing IMP Among Purine Nucleotides The two kinds of vectors (i.e., pDZ-alt and pDZ-alg) prepared according to Example 1 were each individually transformed into the Corynebacterium stationis KCCM-10610 strain (KR Patent No. 10-0588577) by electroporation, and the colonies grown in a selection medium containing kanamycin (25 mg/L) were first selected.

Then, strains, in which the initiation codon of the gene encoding a WhiB family protein is modified to a weakened form (i.e., ATG→TTG or ATG→GTG), were obtained through a secondary cross-over process using a homology between the endogenous gene of the strain and the polynucleotides included in the vectors above.

The strain in which the gene encoding the WhiB family protein is weakened was selected based on mismatch PCR. The 'ATG→TTG' mutation was selected using the primers of SEQ ID NO: 14 and SEQ ID NO: 6, whereas the 'ATG→GTG' mutation was selected using the primers of SEQ ID NO: 15 and SEQ ID NO: 6. Since SEQ ID NO: 14 and SEQ ID NO: 15 each includes T or G at 3' terminus instead of A, which is a nucleotide sequence of the wild-type strain, PCR fragments were allowed to be detected only when there was a mutation. The strains which were confirmed first by mismatch PCR were finally confirmed through sequence analysis of the gene.

Finally, the strains obtained by the above method were named as follows: that is, the strain in which the gene encoding the WhiB family protein is weakened due to the substitution of the initiation codon to a TTG form was named as "CJI-2078"; and the strain in which the above gene is weakened due to the substitution of the initiation codon to a GTG form was named as "CJI-2077".

Example 4-2: Evaluation of Ability of Producing IMP Among Purine Nucleotides of Strain in which WhiB Family Protein is Inactivated In order to measure the IMP-producing ability of the *Corynebacterium stationis* KCCM-10610 strain, which is a strain producing IMP among purine nucleotides, and CJI-2078 and CJI-2077 strains prepared in Example 4-1, the culture method described below was used.

The seed medium below (5 mL) was inoculated into each autoclaved test tube (diameter: 18 mm), cultured with shaking at 30° C. for 24 hours, and the resultant was used as a seed culture solution. A production medium (29 mL) was dispensed into a 250 mL Erlenmeyer flask for shaking, which was autoclaved at 121° C. for 15 minutes, and inoculated with the seed culture solution (2 mL) and cultured for 4 to 5 days. The culture conditions were as follows: revolution rate was set at 170 rpm, the temperature was set at 30° C., and pH was adjusted to 7.5.

The medium compositions used are as follows. The amount of IMP production was measured by a method using HPLC after completion of culture, and the results are shown in Table 5.

IMP Seed Medium

Glucose 10 g/L, Peptone 10 g/L, Meat extract 10 g/L, Yeast extract 10 g/L, NaCl 2.5 g/L, Adenine 100 mg/L, Guanine 100 mg/L, pH 7.2

IMP Flask Production Medium

Monosodium glutamate 1 g/L, Ammonium chloride 10 g/L, Magnesium sulfate 12 g/L, Calcium chloride 0.1 g/L, Iron sulfate 20 mg/L, Manganese sulfate 20 mg/L, Zinc sulfate 20 mg/L, Copper sulfate 5 mg/L, L-cysteine 23 mg/L, Alanine 24 mg/L, Nicotinic acid 8 mg/L, Biotin 45 µg/L, Thiamine HCl 5 mg/L, Adenine 30 mg/L, Phosphoric acid (85%) 19 g/L, Glucose 26 g/L, Fructose 14 g/L (Added)

TABLE 5

| Strain No. | IMP (g/L) |
| --- | --- |
| KCCM-10610 | 11.2 |
| CJI-2078 | 11.7 |
| CJI-2077 | 11.4 |

As shown in Table 5 above, it was confirmed that the amount of IMP production was increased by 0.5 g/L in the CJI-2078 strain and by 0.2 g/L in the CJI-2077 strain, compared to their parent strain (i.e., KCCM-10610). These results confirmed that the amount of IMP production was improved in these strains by 4.5% and 1.8%, respectively, compared to their parent strain.

Example 5: Preparation of Strain in which WhiB Family Protein is Inactivated Using Purine Nucleotide-Producing Mutant Strain, in which Gene of Purine Biosynthetic Pathway is Enhanced, and Evaluation of Purine Nucleotide-Producing Ability of the Same

Example 5-1: Preparation of Strain, in which WhiB Family Protein is Inactivated, Using Mutant Strain Producing IMP Among Purine Nucleotides A strain, in which a WhiB family protein is inactivated, was prepared using an IMP-producing strain, in which a gene of the purine biosynthetic pathway is enhanced. Specifically, the IMP-producing strain, in which a gene of the purine biosynthetic pathway is enhanced, being a modified strain of KCCM-10610 where PurF (i.e., a gene of the purine biosynthetic pathway) is enhanced, is a strain in which the initiation codon of purF gene (i.e., GTG) is converted to ATG. The KCCM-10610 strain, in which the gene of the purine biosynthetic pathway, purF, is enhanced, was named as CJI-1964[KCCM-10610_purF(g1a)]. The CJI-1964 [KCCM-10610_purF(g1a)] strain was transformed with the two kinds of vectors (i.e., pDZ-alt and pDZ-alg) prepared in Example 1, by electroporation, and strains in which the initiation codon of the gene encoding the WhiB family protein was modified to a weakened form (i.e., ATG→TTG or ATG→GTG), were obtained in the same manner as in Example 4-1.

Finally, the strains obtained by the above method were named as follows: that is, the strain in which the gene encoding the WhiB family protein is weakened due to the substitution of the initiation codon to a TTG form was named as "CJI-2081"; and the strain in which the above gene is weakened due to the substitution of the initiation codon to a GTG form was named as "CJI-2080".

Example 5-2: Evaluation of Ability of Producing IMP Among Purine Nucleotides of Strain in which WhiB Family Protein is Inactivated In order to measure the IMP-producing abilities of the CJI-1964 strain, in which a gene of the purine biosynthetic pathway is enhanced, and the CJI-2081 and CJI-2080 strains prepared in Example 5-1, the culture method as in Example 4-2 was used. After completion of culture, the amount of IMP production in each strain was measured by a method using HPLC, and the results are shown in Table 6 below.

TABLE 6

| Strain No. | IMP (g/L) |
| --- | --- |
| CJI-1964 | 11.4 |
| CJI-2081 | 12.3 |
| CJI-2080 | 12.1 |

As shown in Table 6 above, it was confirmed that the amount of IMP production was increased by 0.9 g/L in the CJI-2081 strain and by 0.7 g/L in the CJI-2080 strain, compared to their parent strain (i.e., CJI-1964). These results confirmed that the amount of IMP production was improved in these strains by 7.8% and 6.1%, respectively, compared to their parent strain.

That is, it was confirmed that when a WhiB family protein transcriptional regulator is inactivated in a strain, the strain can produce purine nucleotides in higher yield compared to its parent strain or other non-modified microorganisms. Additionally, these results imply that when the WhiB family protein is inactivated in a strain, the strain can produce purine nucleotides in higher yield compared to its parent strain or other non-modified microorganisms.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. *Corynebacterium stationis* producing a purine nucleotide, wherein a protein consisting of an amino acid sequence of SEQ ID NO: 1 is inactivated.

2. The *Corynebacterium stationis* according to claim 1, wherein the purine nucleotide is at least one purine nucleotide selected from 5'-inosine monophosphate (IMP), 5'-xanthosine monophosphate (XMP), 5'-guanosine monophosphate (GMP), and 5'-adenylic acid (AMP).

3. The *Corynebacterium stationis* according to claim 1, wherein in the *Corynebacterium stationis*, a biosynthetic pathway of a purine nucleotide is further enhanced.

4. The *Corynebacterium stationis* according to claim 3, wherein the enhancement of a biosynthetic pathway of a purine nucleotide is the enhancement of an activity of the amidophosphoribosyltransferase (PurF) protein.

5. A method for producing a purine nucleotide, comprising culturing the *Corynebacterium stationis* according to claim 1 in a medium.

6. The method according to claim 5, wherein the purine nucleotide is at least one purine nucleotide selected from 5′-inosine monophosphate (IMP), 5′-xanthosine monophosphate (XMP), 5′-guanosine monophosphate (GMP), and 5′-adenylic acid (AMP).

7. The method according to claim 5, further comprising recovering a purine nucleotide from the cultured *Corynebacterium stationis* or the medium after the culture.

8. A method for increasing the production of a purine nucleotide, comprising inactivating a protein consisting of an amino acid sequence of SEQ ID NO: 1 in a microorganism of the genus *Corynebacterium*.

* * * * *

UNITED STATES PATENT AND TRADEMARK OFFICE
CERTIFICATE OF CORRECTION

| | |
|---|---|
| PATENT NO. | : 11,421,200 B2 |
| APPLICATION NO. | : 16/960449 |
| DATED | : August 23, 2022 |
| INVENTOR(S) | : Hee Ju Kim et al. |

It is certified that error appears in the above-identified patent and that said Letters Patent is hereby corrected as shown below:

On the Title Page

Item (56) References Cited/U.S. Patent Documents should read:
--11,008,599 B2 05/2021 Lee et al.--

Signed and Sealed this
Eleventh Day of October, 2022

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 121
<212> TYPE: PRT
<213> ORGANISM: Corynebacterium sp.

<400> SEQUENCE: 1

Met Arg Leu Cys Val Asp Lys Gln Lys Glu Arg Gln Met Thr Val Ser
1               5                   10                  15

Leu Lys Met Ser Thr Gln Ala Asp Thr Tyr Asn Ala Thr Thr Pro Glu
            20                  25                  30

Arg Gly Glu Trp Val Thr Gln Ala Lys Cys Arg Asn Gly Asp Pro Asp
        35                  40                  45

Ala Leu Phe Val Arg Gly Ala Glu Gln Arg Lys Ala Ala Val Ile Cys
    50                  55                  60

Arg His Cys Pro Val Leu Asn Glu Cys Arg Ala Asp Ala Leu Asp Asn
65                  70                  75                  80

Arg Val Glu Phe Gly Val Trp Gly Gly Leu Thr Glu Arg Gln Arg Arg
                85                  90                  95

Ala Leu Leu Arg Lys Asn Pro His Ile Thr Asn Trp Ala Asp Tyr Leu
            100                 105                 110

Ala Gln Gly Gly Glu Leu Glu Gly Ile
        115                 120

<210> SEQ ID NO 2
<211> LENGTH: 366
<212> TYPE: DNA
<213> ORGANISM: Corynebacterium sp.

<400> SEQUENCE: 2
atgagattat gtgtggataa gcagaaggag cgccagatga ccgtgagctt gaagatgtca      60
actcaggcgg acacctacaa tgcgacaacc ccagaacgcg gggagtgggt gacgcaagct     120
aagtgtcgaa atggtgaccc tgatgcactt tttgtgcgcg gtgcggagca gcgtaaagct     180
gccgttattt gccgtcactg tcctgtcctt aatgaatgtc gagcagatgc tctagataac     240
cgcgtggaat tcggtgtctg gggcggacta actgagcgcc agcgccgtgc gttgctgcgc     300
aaaaacccac acatcactaa ctgggctgat tatctcgccc aaggtggaga actagaagga     360
atctaa                                                                366

<210> SEQ ID NO 3
<211> LENGTH: 32
<212> TYPE: DNA
<213> ORGANISM: Artificial Sequence
<220> FEATURE:
<223> OTHER INFORMATION: Primer sequence
```

<400> SEQUENCE: 3
tgctctagag atctagcacg cctaaagagt cg                                32

<210> SEQ ID NO 4
<211> LENGTH: 20
<212> TYPE: DNA
<213> ORGANISM: Artificial Sequence
<220> FEATURE:
<223> OTHER INFORMATION: Primer sequence

<400> SEQUENCE: 4
gtaggtgtcc gcctgagttg                                              20

<210> SEQ ID NO 5
<211> LENGTH: 44
<212> TYPE: DNA
<213> ORGANISM: Artificial Sequence
<220> FEATURE:
<223> OTHER INFORMATION: Primer sequence

<400> SEQUENCE: 5
caactcaggc ggacacctac tcactaactg ggctgattat ctcg                   44

<210> SEQ ID NO 6
<211> LENGTH: 29
<212> TYPE: DNA
<213> ORGANISM: Artificial Sequence
<220> FEATURE:
<223> OTHER INFORMATION: Primer sequence

<400> SEQUENCE: 6
tgctctagag gtgcccttca tcatcaggt                                    29

<210> SEQ ID NO 7
<211> LENGTH: 31
<212> TYPE: DNA
<213> ORGANISM: Artificial Sequence
<220> FEATURE:
<223> OTHER INFORMATION: Primer sequence

<400> SEQUENCE: 7
cgcggatccc agccattagg taaggtgctt g                                 31

<210> SEQ ID NO 8
<211> LENGTH: 20
<212> TYPE: DNA
<213> ORGANISM: Artificial Sequence
<220> FEATURE:
<223> OTHER INFORMATION: Primer sequence

<400> SEQUENCE: 8
agaggcgtat tcacgctctg                                              20

<210> SEQ ID NO 9
<211> LENGTH: 46
<212> TYPE: DNA
<213> ORGANISM: Artificial Sequence
<220> FEATURE:
<223> OTHER INFORMATION: Primer sequence

<400> SEQUENCE: 9
cagagcgtga atacgcctct tgagattatg tgtggataag cagaag                 46

<210> SEQ ID NO 10

```
<211> LENGTH: 29
<212> TYPE: DNA
<213> ORGANISM: Artificial Sequence
<220> FEATURE:
<223> OTHER INFORMATION: Primer sequence

<400> SEQUENCE: 10
cgcggatccc gaggatacaa agcccacga                                     29

<210> SEQ ID NO 11
<211> LENGTH: 20
<212> TYPE: DNA
<213> ORGANISM: Artificial Sequence
<220> FEATURE:
<223> OTHER INFORMATION: Primer sequence

<400> SEQUENCE: 11
cgaggcgtat tcacgctctg                                               20

<210> SEQ ID NO 12
<211> LENGTH: 46
<212> TYPE: DNA
<213> ORGANISM: Artificial Sequence
<220> FEATURE:
<223> OTHER INFORMATION: Primer sequence

<400> SEQUENCE: 12
cagagcgtga atacgcctcg tgagattatg tgtggataag cagaag                  46

<210> SEQ ID NO 13
<211> LENGTH: 21
<212> TYPE: DNA
<213> ORGANISM: Artificial Sequence
<220> FEATURE:
<223> OTHER INFORMATION: Primer sequence

<400> SEQUENCE: 13
catgttgttg ccctcggaat c                                             21

<210> SEQ ID NO 14
<211> LENGTH: 15
<212> TYPE: DNA
<213> ORGANISM: Artificial Sequence
<220> FEATURE:
<223> OTHER INFORMATION: Primer sequence

<400> SEQUENCE: 14
cgtgaatacg cctct                                                    15

<210> SEQ ID NO 15
<211> LENGTH: 15
<212> TYPE: DNA
<213> ORGANISM: Artificial Sequence
<220> FEATURE:
<223> OTHER INFORMATION: Primer sequence

<400> SEQUENCE: 15
cgtgaatacg cctcg                                                    15
```